United States Patent
Mu et al.

(10) Patent No.: US 7,862,556 B2
(45) Date of Patent: Jan. 4, 2011

(54) SURGICAL SYSTEM THAT ABLATES SOFT TISSUE

(75) Inventors: Liyue Mu, Fremont, CA (US); Ming Lai, Rochester, NY (US); Kangze Cai, Fremont, CA (US); Weiguo Luo, Fremont, CA (US)

(73) Assignee: Applied Harmonics Corporation, Fremont, CA (US)

( * ) Notice: Subject to any disclaimer, the term of this patent is extended or adjusted under 35 U.S.C. 154(b) by 966 days.

(21) Appl. No.: 11/454,828

(22) Filed: Jun. 19, 2006

(65) Prior Publication Data

US 2007/0038207 A1 Feb. 15, 2007

Related U.S. Application Data

(60) Provisional application No. 60/691,528, filed on Jun. 17, 2005.

(51) Int. Cl.
*A61B 18/04* (2006.01)
(52) U.S. Cl. .............. 606/10; 219/121.68; 219/161.69
(58) Field of Classification Search ............ 606/3, 606/4, 5, 11, 10; 372/26, 10; 219/121.68, 219/121.69
See application file for complete search history.

(56) References Cited

U.S. PATENT DOCUMENTS

| | | | |
|---|---|---|---|
| 4,675,872 A | 6/1987 | Popek et al. ............... 372/10 |
| 5,066,291 A | 11/1991 | Stewart ...................... 606/3 |
| 5,151,909 A | 9/1992 | Davenport et al. ........... 372/22 |
| 5,312,396 A | 5/1994 | Feld et al. | |
| 5,776,175 A | 7/1998 | Eckhouse et al. ........... 607/100 |
| 5,805,622 A | 9/1998 | Brinkmann ................. 372/9 |
| 6,009,110 A | 12/1999 | Wiechmann et al. ......... 372/10 |
| 6,031,854 A | 2/2000 | Ming ........................ 372/22 |
| 6,038,241 A | 3/2000 | Von Elm et al. | |
| 6,156,030 A * | 12/2000 | Neev ........................ 606/10 |
| 6,309,352 B1 | 10/2001 | Oraevsky et al. ........... 600/407 |
| 6,413,267 B1 | 7/2002 | Dumoulin-White et al. ... 607/89 |
| 6,482,199 B1 * | 11/2002 | Neev ........................ 606/10 |

(Continued)

OTHER PUBLICATIONS

Malek et al., "High-Power Potassium-Titanyl-Phosphate (KTP/532) Laser Vaporization Prostatectomy: 24 Hours Later", *Urology*, vol. 51, 1998, Elsevier Science Inc., pp. 254-256.

(Continued)

*Primary Examiner*—Henry M Johnson, III
*Assistant Examiner*—Jeffrey B Lipitz
(74) *Attorney, Agent, or Firm*—Pillsbury Winthrop Shaw Pittman LLP

(57) ABSTRACT

A surgical system that ablates soft tissue. The system may include a fiber laser oscillator as the gain medium that emits electromagnetic radiation. The system may process the electromagnetic radiation, and direct the electromagnetic radiation on to the soft tissue to be ablated. Due at least in part to the nature of the electromagnetic radiation emitted by the fiber laser oscillator, the system may provide various enhancements, such as a higher power conversion efficiency, a longer lifetime, less heat dissipation, a more compact design, and/or other enhancements, for example. The system may also generate electromagnetic radiation with a relatively high beam quality. This may reduce beam divergence and beam spot size on targeted soft tissue, thereby enhancing power density in the electromagnetic radiation guided to the soft tissue. This enhanced power density may facilitate effective ablation.

17 Claims, 5 Drawing Sheets

U.S. PATENT DOCUMENTS

| | | | |
|---|---|---|---|
| 6,554,824 B2 | 4/2003 | Davenport et al. | 606/3 |
| 6,723,090 B2 * | 4/2004 | Altshuler et al. | 606/9 |
| 6,986,764 B2 | 1/2006 | Davenport et al. | 606/3 |
| 2001/0031960 A1 * | 10/2001 | Kliewer et al. | 606/5 |
| 2003/0058403 A1 | 3/2003 | Lai et al. | 351/212 |
| 2003/0130649 A1 | 7/2003 | Murray et al. | 606/3 |
| 2003/0135205 A1 | 7/2003 | Davenport et al. | 606/3 |
| 2003/0156605 A1 * | 8/2003 | Richardson et al. | 372/25 |
| 2004/0022280 A1 | 2/2004 | Lai et al. | 372/5 |
| 2004/0134894 A1 * | 7/2004 | Gu et al. | 219/121.68 |
| 2004/0236319 A1 | 11/2004 | Davenport et al. | 606/3 |
| 2005/0027286 A1 | 2/2005 | Davenport et al. | 606/3 |
| 2005/0092720 A1 * | 5/2005 | Gu et al. | 219/121.69 |
| 2005/0256513 A1 | 11/2005 | Murray et al. | 606/3 |
| 2005/0288653 A1 | 12/2005 | Lai et al. | 606/10 |
| 2006/0007965 A1 * | 1/2006 | Tankovich et al. | 372/10 |

OTHER PUBLICATIONS

Randall S. Kuntzman et al., "High-Power Potassium Titanyl Phosphate Laser Vaporization Prostatectomy", *Mayo Clinic Proc.*, vol. 73, 1998, pp. 798-801.

R. S. Malek et al., "High Power Potassium-Titanyl-Phosphate Laser Vaporization Prostatectomy", *The Journal of Urology*, vol. 163, Jun. 2000, pp. 1730-1733.

Mahmood A. Hai et al., "Photoselective Vaporization of the Prostate: Initial Experience with a New 80 W KTP Laser for the Treatment of Benign Prostatic Hyperplasia", *Journal of Endourology*, vol. 17, No. 2, Mar. 2003, pp. 93-96.

Walter Koechner, "Solid-State Laser Engineering", $5^{th}$ Edition, Springer-Verlag Berlin Heidelerg, New York, 1999, 12 pages.

Anthony E. Siegman, "Lasers", University Science Books, Mill Valley, California, 1986, 26 pages.

"Photoselective Vaporization of the Prostate", *Supplement to Urology Times*, vol. 30, Supplement 1, May 2002, 20 pages.

Randall S. Kuntzman et al., "High-Power (60-Watt) Potassium-Titanyl-Phosphate Laser Vaporization Prostatectomy in Living Canines and in Human and Canine Cadavers", *Urology*, vol. 49, No. 5, 1997, Elsevier Science Inc., pp. 703-708.

Alfred Vogel et al., "Mechanisms of Pulsed Laser Ablation of biological Tissues", *Chem. Rev.*, vol. 103, Published on Web Feb. 12, 2003, pp. 577-644.

Tuan Vo-Dinh, "Biomedical Photonics Handbook", CRC Press, 2003, pp. 2-1 to 2-75, 5-1 to 5-16.

V. V, Golovlyov et al., "Ablation of an Optically Homogeneous Absorbing Medium by Scattered Pulsed Laser Radiation", *Applied Physics B*, vol. 57, 1993, p. 451.

R. O. Esenaliev et al., "Laser Ablation of Aqueous Solutions with Spatially Homogeneous and Heterogeneous Absorption", *Applied Physics B*, vol. 59, 1994, p. 73.

Lawrence Livermore National Lab, "The Short-Pulse Laser: A Safe, Painless Surgical Tool", *Science & Technology Review*, Oct. 1995, 3 pages.

V. Venugopalan et al., "Thermodynamic Response of Soft Biological Tissues to Pulsed Infrared-Laser Irradiation", *Biophysical Journal*, vol. 70. Jun. 1996, pp. 2981-2993.

M. Ogura et al., "Myocardium Tissue Ablation with High-Peak-Power Nanosecond 1,064- and 532-nm Pulsed Lasers: Influence of Laser-Induced Plasma", *Lasers in Surgery and Medicine*, vol. 31, 2002, pp. 136-141.

J. Niamtu, "Clinical Applications of the 532-nm Diode Laser for the Treatment of Facial Telangiectasia and Pigmented Lesions: Literature Review, History, and Discussion of Clinical Experience", *The American Journal of Cosmetic Surgery*, vol. 18, No. 2, 2001, pp. 71-81.

S. Uhlhorn, "Free Electron Laser Ablation of Soft Tissue: The Effects of Chromophore and Pulse Characteristics of Ablation Mechanics", *Ph.D. Dissertation*, Vanderbilt University, Aug. 2002, 113 pages.

A. F. El-Sherif and T. A, King, "Soft and Hard Tissue Ablation with Short-Pulse High Peak Power and Continuous Thulium-Silica Fibre Lasers", *Lasers Med. Sci*, vol. 18, No. 3, 2003, pp. 139-147.

A. Liu et al., 60-W Green Output by Frequency Doubling of a Polarized Yb-Doped Fiber Laser, *Optics Letters*, vol. 30, No. 1, Jan. 1, 2005, pp. 67-69.

F. H. Loesel et al., "Laser-Induced Optical Breakdown on Hard and Soft Tissues and Its Dependence on the Pulse Duration: Experiment and Model", *IEEE Journal of Quantum Electronics*, vol. 32, No. 10, Oct. 1996, pp. 1717-1722.

F. Sengor et al, "A Comparative Study of Laser Ablation and Transurethral Electroresection for Benign Prostatic Hyperplasia; Results of a 6-Month Follow-Up", *British Journal of Urology*, vol. 78, Issue 3, 1996, pp. 398-400.

M. Grasso et al. "Lasers in Urology", http://www.emedicine.com/med/topic3037.htm, Mar. 2006, 15 pages.

J. Berger et al, "370 mW, 1:06 µm, CW $TEM_{00}$ Output from an Nd:YAG Laser Rod End-Pumped by a Monolithic Diode Array", Apr. 13, 1987, *Electronics Letters*, vol. 23, No. 13, Jun. 18, 1987, pp. 669-670.

\* cited by examiner

SURGICAL SYSTEM THAT ABLATES SOFT TISSUE

CROSS-REFERENCE TO RELATED APPLICATIONS

This application claims the benefit of U.S. Provisional Application entitled "Apparatus and Method for Soft Tissue Ablation Employing High Power Harmonic Fiber Laser" No. 60/691,528 filed Jun. 17, 2005, the entire content of which is hereby incorporated by reference.

FIELD OF THE INVENTION

The invention relates to laser soft tissue ablation and in particular to laser prostatectomy.

BACKGROUND OF THE INVENTION

Benign Prostatic Hyperplasia (BPH) can cause urinary frequency, dysuria and incomplete bladder emptying. The surgical "gold standard" for treating BPH has been the transurethral electrosurgical resection of obstructing prostatic tissue. Since its introduction some 50 years ago, transurethral resection of the prostate (TURP) has become the most widely used surgical therapy for BPH. Unfortunately, TURP associates with numerous side effects.

In the past decade, laser prostate surgery has become an alternative option to treat BPH, which troubles effected men with symptoms such as urinary frequency, dysuria and incomplete bladder emptying. In laser prostate surgery, a high power laser beam may be delivered to target prostate tissue through an optical fiber that is introduced through an endoscope or cystoscope. The effectiveness of this treatment for BPH (or for the removal of other soft tissue) may depend on a number of factors, including wavelength, power density, pulse duration, pulse fluence and/or other factors.

Conventional laser ablation systems implemented in laser prostate surgery may include high average power (60-80 W) Nd:YAG laser with a wavelength of 1064 nm. The electromagnetic radiation emitted by these systems may heat up the laser-irradiated tissue to boiling temperature. This may evaporate a top layer of the tissue and coagulate an under layer of the tissue. The conventional systems tend to employ Nd:YAG lasers because they may be capable of emitting electromagnetic radiation with an enhanced hemostatic effect. For example, the radiation may penetrate the tissue to a 7 mm penetration depth. But, with the Nd:YAG systems, this penetration may create a thick layer of tissue coagulation. For this and other reasons, conventional systems employing an Nd:YAG laser may not be as effective as TURP in the treatment of obstructive BPH.

Other conventional systems for ablating soft tissue, such as prostate tissue have implemented high power (60-100 W) Ho:YAG lasers with a wavelength of 2140 nm. Electromagnetic radiation produced by these systems may by absorbed by water, and can thus evaporate soft tissue effectively. Under limited circumstances, Ho:YAG laser surgery may produce a clinical outcome comparable with TURP. However, Ho:YAG laser surgery may provide various technical problems, and may not currently be practical for widespread usage.

In still other conventional systems, a 60 W average power, Q-switched and frequency-doubled Nd:YAG laser may be used for the ablation of soft tissue in BPH treatment. In these systems, the laser may be lamp pumped to produce quasi-CW Q-switched pulses at 532 nm. Electromagnetic radiation at this wavelength is transparent in water but may be selectively absorbed by oxyhemoglobin in soft tissue. These systems may effectively vaporize and ablate soft tissue and concurrently achieve some level of hemostasis. The surgical outcome is comparable with TURP while the complication is significantly reduced. However, as with the Ho:YAG systems, technical problems with the implementation of an Nd:YAG laser in a clinical system for ablating soft tissue exist.

For example, the power conversion efficiency of these systems may be relatively low. In some instances, this efficiency may be below 3%. This may require these systems to include a special power source, as they may not be efficient enough to run off of a power supply provided by a standard wall outlet (e.g. a 110V outlet, a 220V outlet, etc.).

As another example, Nd:YAG lasers, as well as the Ho:YAG lasers, typically implement a solid state gain medium, which may dissipate an elevated amount of energy as heat. Thus, in order to avoid damaging components of the laser ablation systems that employ these types of lasers, the systems usually must incorporate an extensive cooling system. For example, these cooling systems may include liquid cooling systems and/or secondary cooling loops. These extensive cooling systems may require additional power, be bulky and/or unwieldy, an/or provide other drawbacks.

Other drawbacks associated with these and other conventional systems that use lasers to ablate soft tissue exist.

SUMMARY

One aspect of the invention relates to a surgical system that ablates soft tissue. The system may include a fiber laser oscillator as the gain medium that emits electromagnetic radiation. The system may process the electromagnetic radiation, and direct the electromagnetic radiation on to the soft tissue to be ablated. Due at least in part to the nature of the electromagnetic radiation emitted by the fiber laser oscillator, the system may provide various enhancements, such as a higher power conversion efficiency, a longer lifetime, less heat dissipation, a more compact design, and/or other enhancements, for example. The system may also generate electromagnetic radiation with a relatively high beam quality. This may reduce beam divergence and beam spot size on targeted soft tissue, thereby enhancing power density in the electromagnetic radiation guided to the soft tissue. This enhanced power density may facilitate effective ablation.

In some embodiments of the invention, the surgical system may include a source, an output assembly, a power assembly, a cooling assembly, a processor, and/or other components. In some implementations, the source may output electromagnetic radiation at a predetermined output wavelength and a predetermined output power. The output assembly may be configured to deliver the output electromagnetic radiation to soft tissue of a patient to ablate the soft tissue. For example, output assembly may include an optical fiber. In some instances, the optical fiber may include a side-firing tip. The power assembly may receive an input power from an external power source and may, at least in part, drive source and/or other components of the surgical system with the input power. The cooling assembly may cool the source during operation. The processor may control operation of the various components of the system.

According to various embodiments of the invention, the source may include a generation assembly, an amplification assembly, a wavelength adjustment assembly, and/or other components or assemblies. The generation assembly may generate electromagnetic radiation at a predetermined fundamental wavelength and a predetermined fundamental power. The amplification assembly may be optically coupled with the generation assembly to receive electromagnetic radiation from the generation assembly, and may amplify the power of the received electromagnetic radiation to ensure that the electromagnetic radiation that is output from the source at the predetermined output power. The wavelength adjustment assembly may be optically coupled to the amplification assembly, and may adjust the wavelength of electromagnetic radiation received from the amplification assembly to the predetermined output wavelength. In some instances, the output wavelength may be shorter than the fundamental wavelength.

In some implementations, the generation assembly may include one or more pump sources, a fiber laser oscillator, an amplitude modulator, and/or other components. The pump source may provide pump energy to fiber laser oscillator. The pump energy may cause the fiber laser oscillator to lase, thereby emitting electromagnetic radiation with the fundamental wavelength. The amplitude modulator may be optically coupled to the fiber laser oscillator to receive electromagnetic radiation emitted by the fiber laser oscillator. The amplitude modulator may modulate the amplitude of the received electromagnetic radiation to provide electromagnetic radiation in pulses. The pulses of electromagnetic radiation may be provided at a predetermined frequency and/or with a predetermined pulse width. Since the amplitude modulator modulates only the amplitude of the electromagnetic radiation, electromagnetic radiation included in the pulses provided by the amplitude modulator may generally have the fundamental wavelength. The electromagnetic radiation included in the pulses created by the amplitude modulator may have the fundamental power.

According to various implementations, the wavelength adjustment assembly may act as a second harmonics generator by receiving electromagnetic radiation from the amplification assembly and adjusting the wavelength of the received electromagnetic radiation from the fundamental wavelength to the output wavelength. In some instances, the wavelength adjustment assembly may effectively half the wavelength (e.g., double the frequency) of the received electromagnetic radiation.

In some embodiments of the invention, the surgical system may process the electromagnetic radiation emitted by the fiber laser oscillator to output green electromagnetic radiation (e.g., electromagnetic radiation with a wavelength of about 540 nm). The pulses of electromagnetic radiation, as provided by the amplitude modulator may cause the output electromagnetic radiation to be output in a quasi-continuous mode. Both blood contained soft tissue and coagulated soft tissue may experience good optical absorption for green electromagnetic radiation.

As the fiber laser oscillator lases during the operation of the surgical system, it may produce electromagnetic radiation at a wavelength of about 1080 nm that has a relatively high beam quality (e.g., substantially single transverse mode (TEM00) radiation) with an enhanced input power to optical output power efficiency, particularly when compared with other, more conventional oscillator media (e.g., solid state gain media, etc.). This may prove useful in the context of soft tissue ablation for several reasons.

For instance, electromagnetic radiation with a high beam quality may enhance soft tissue ablation, so the generation of electromagnetic radiation by the fiber laser oscillator with substantially a single transverse mode and at a relatively high power conversion efficiency may enable the source to generate electromagnetic radiation that is effective in ablating soft tissue while being powered only from a standard wall outlet. This may facilitate the implementation of the surgical system for soft tissue ablation in a variety of treatment settings where more substantial power supplies may not be readily available (e.g., in a hospital, a doctors office, a patients home, etc.).

As another example of an enhancement provided by the use of the fiber laser oscillator, the source may not dissipate as much energy in the form of heat as with other conventional laser ablation systems. In other systems used for soft tissue ablation and employing a more standard oscillating medium, the amount of heat produced as a bi-product may require an extensive cooling system to ensure that theses systems are not damaged by the heat (e.g., they may require liquid cooling and/or a secondary cooling loop). The implementation of the fiber laser oscillator in the surgical system may enable the cooling assembly to keep the various components of the system at safe operating temperatures without employing a liquid cooling system and/or a secondary cooling loop. This may reduce the overall size and weight of the system, and therefore make the use of the system more convenient.

The use of the amplification assembly in conjunction with the fiber laser oscillator may further enhance the power conversion efficiency of the system in providing electromagnetic radiation for ablating soft tissue. In some implementations, the fiber laser oscillator in conjunction with the amplification assembly may convert the input power used by the power assembly to power the surgical system to optical power output to the patient in the form of electromagnetic radiation with an efficiency of greater than about 6%. In some of these implementations, the input power may be converted with an efficiency of between about 8% and about 14%.

These and other objects, features, benefits, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION

Figure 1:
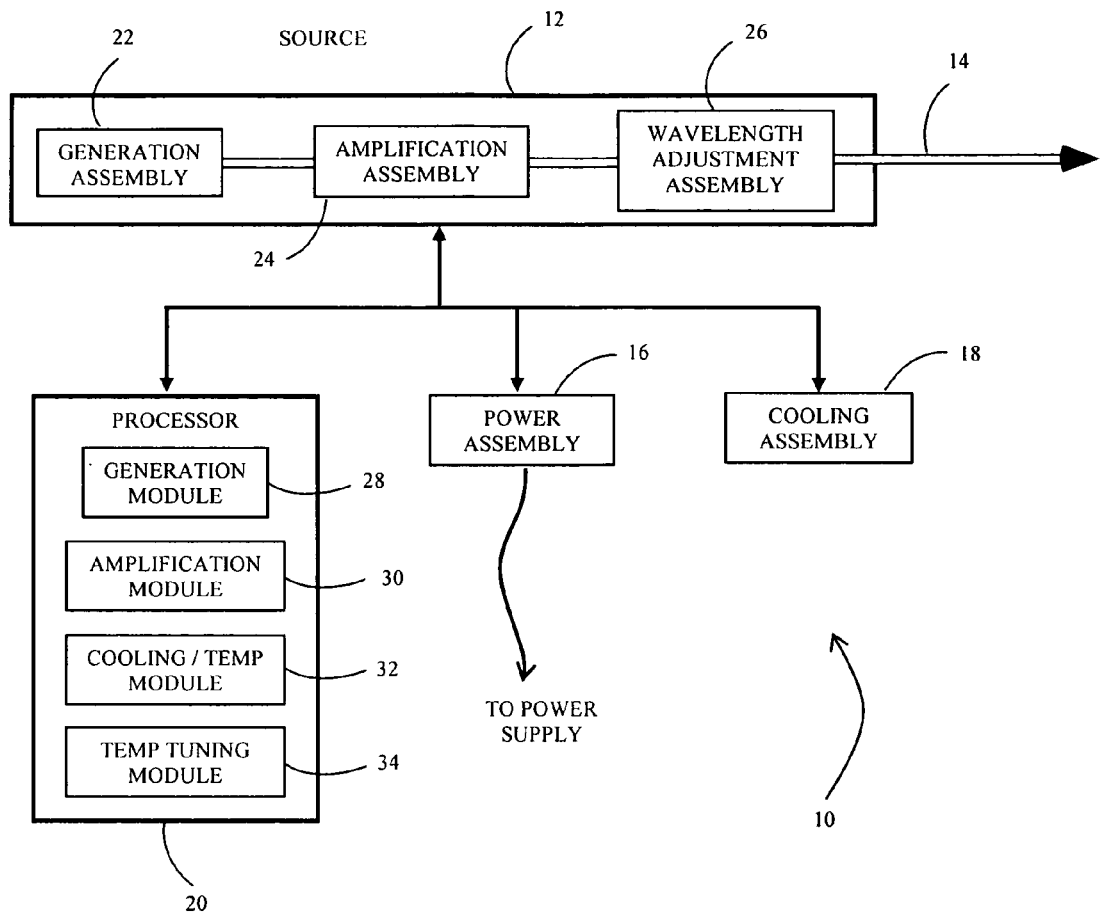
FIG. 1 illustrates a surgical system, according to one or more embodiments of the invention.

FIG. 1 illustrates a surgical system 10 configured to ablate soft tissue of a patient, according to one or more implementations. Surgical system 10 may be particularly configured to ablate prostate tissue, or other soft tissue. In some implementations, system 10 may include a source 12, an output assembly 14, a power assembly 16, a cooling assembly 18, a processor 20, and/or other components. In some implementations, source 12 may output electromagnetic radiation at a predetermined output wavelength and a predetermined output power. Output assembly 14 may be configured to deliver the output electromagnetic radiation to soft tissue of the patient to ablate the soft tissue. For example, output assembly 14 may include an optical fiber. In some instances, the optical fiber may include a side-firing tip. Output assembly 14 may be configured to deliver the output electromagnetic radiation to prostate tissue of the patient to ablate the prostate tissue. Power assembly 16 may receive an input power from an external power source and may, at least in part, drive source 12 and/or other components of system 10 with the input power. Cooling assembly 18 may cool source 12 during operation. Processor 20 may control operation of system 10.

As is illustrated in FIG. 1, source 12 may include a generation assembly 22, an amplification assembly 24, a wavelength adjustment assembly 26, and/or other components or assemblies. Generation assembly 22 may generate electromagnetic radiation at a predetermined fundamental wavelength and a predetermined fundamental power. Amplification assembly 24 may be optically coupled with generation assembly 22 to receive electromagnetic radiation from generation assembly 22 and may amplify the power of the received electromagnetic radiation to that the electromagnetic radiation that is output to ablate the soft tissue will be output at the predetermined output power. Wavelength adjustment assembly 26 may be optically coupled to amplification assembly 24, and may adjust the wavelength of the received electromagnetic radiation to the predetermined output wavelength. In some instance, the output wavelength may be shorter than the fundamental wavelength.

In some implementations, processor 20 may execute a generation module 28, an amplification module 30, a cooling/temperature module 32, a temperature tuning module 34, and/or other modules. Although processor 20 is shown in FIG. 1 as a single unit, it may be appreciated that processor 20 may include a plurality of processors operatively linked to each other, and that various ones of the linked processors may be physically located locally to each other, or may be remote from each other. For example, in one implementation, processor 20 may include a processor integral with the other components system 10 and a central processing unit of a host computer system being employed to control and/or read out data from system 10. In another implementation, processor 20 may include only the processor formed integrally with the other components of system 10. Other configurations exist. Further, each of modules 28, 30, 32, and/or 34 may be implemented in hardware, software, firmware, or in some combination thereof. Modules 28, 30, 32, and/or 34 may be executed locally to each other, or one or more of modules 28, 30, 32, and/or 34 may be executed remotely from other ones of modules 28, 30, 32, and/or 34.

Generation module 28 may operate to control and receive feedback from generation assembly 22. For instance, as will be discussed further below, generation module 28 may include one or more drivers configured to communicate with various components of generation assembly 22.

Amplification module 30 may operate to control and receive feedback from amplification assembly 24. For instance, as will be discussed further below, amplification module 30 may include one or more drivers configured to communicate with various components of amplification assembly 30.

Cooling/temperature module 32 may operate to determine one or more temperature related to the operation of system 10. For example, cooling/temperature module 32 may receive information from one or more sensors (not shown) located at source 12, and based on this information may determine an overall temperature of source 12, individual temperatures of one or more of assemblies 22, 24, or 26, and/or individual temperatures of one or more components of assemblies 22, 24, or 26. Further, cooling/temperature module 32 may be operate to control and/or receive feedback from cooling assembly 18.

As will be discussed further below, temperature tuning module 34 may operate to tune one or more components of wavelength adjustment module 26 to an operating temperature. The tuning performed by temperature tuning module 34 may enhance the performance of wavelength adjustment assembly 26, protect one or more of the components of wavelength adjustment assembly 26, and/or provide other advantages.

Figure 2:
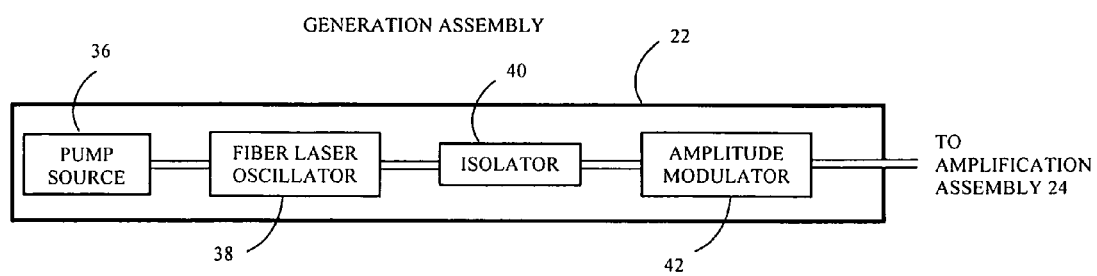
FIG. 2 illustrates a generation assembly, according to one or more embodiments of the invention.

Referring to FIG. 2, generation assembly 22 is illustrated in accordance with one or more implementations. As shown, generation assembly 22 may include one or more pump sources 36, a fiber laser oscillator 38, an optical isolator 40, an amplitude modulator 42, and/or other components. Pump source 36 may provide pump energy to fiber laser oscillator 38. The pump energy may cause fiber laser oscillator 38 to lase, thereby emitting electromagnetic radiation with the fundamental wavelength. Amplitude modulator 42 may be optically coupled to fiber laser oscillator 38, via optical isolator 40, to receive electromagnetic radiation emitted by fiber laser oscillator 38. Amplitude modulator 42 may modulate the amplitude of the received electromagnetic radiation to provide electromagnetic radiation in pulses. The pulses of electromagnetic radiation may be provided at a predetermined frequency and/or with a predetermined pulse width. Since amplitude modulator 42 modulates only the amplitude of the electromagnetic radiation, electromagnetic radiation included in the pulses provided by amplitude modulator 42 may generally have the fundamental wavelength. The electromagnetic radiation included in the pulses of amplitude modulator 42 may have the fundamental power.

Pump source 26 may be controlled by a pump driver executed by generation module 28 (as shown in FIG. 1). Pump source 36 may include one or more diode lasers that emit electromagnetic radiation. The electromagnetic radiation emitted by the one or more diode lasers may be guided to fiber laser oscillator 38, and may provide the pump energy requisite to lase fiber laser oscillator 38. In some instances, the one or more diode lasers may include a plurality of broad-area laser diodes. The broad-area laser diodes may emit electromagnetic radiation with a wavelength between about 915 nm and 976 nm. In some implementations, fiber laser oscillator 38 may include a double or triple clad fiber to enable the energy from pump source 36 to be applied to fiber laser oscillator 38 as a cladding pump. It should be appreciated that alternative configurations of pump source 36 are also contemplated.

As fiber laser oscillator 38 lases, it may produce electromagnetic radiation at a wavelength of about 1080 nm that has a relatively high beam quality (e.g., substantially single transverse mode (TEM00) radiation) with an enhanced input power to optical output power efficiency, particularly when compared with other, more conventional oscillator media (e.g., solid state gain media, etc.). This may prove useful in the context of soft tissue ablation for several reasons.

For instance, electromagnetic radiation with a high beam quality may enhance soft tissue ablation, so the generation of electromagnetic radiation by fiber laser oscillator 38 with substantially a single transverse mode and at a relatively high power conversion efficiency may enable source 12 to generate electromagnetic radiation that is effective in ablating soft tissue while being powered only from a standard wall outlet via power assembly 16. This may facilitate the implementation of system 10 for soft tissue ablation in a variety of treatment settings where more substantial power supplies may not be readily available (e.g., in a hospital, a doctors office, a patients home, etc.).

As another example of an enhancement provided by the use of fiber laser oscillator 38, source 12 may not dissipate as much energy in the form of heat. In other systems used for soft tissue ablation that employ a more standard oscillating medium, the amount of heat produced as a bi-product may require an extensive cooling system to ensure that theses systems are not damaged by the dissipated heat (e.g., they may require liquid cooling and/or a secondary cooling loop). The implementation of fiber laser oscillator 38 in system 10 may enable cooling assembly 18 to keep the various components of system 10 at safe operating temperatures without employing a liquid cooling system and/or a secondary cooling loop. This may reduce the overall size and weight of system 10, and therefore make the use of system 10 more convenient.

Fiber laser oscillator 38 may include a Yb-doped fiber, or other types of fiber laser oscillators, as the oscillator. The electromagnetic radiation emitted by fiber laser oscillator 38 may be near infrared. For example, the electromagnetic radiation may have a wavelength of between about 1000 nm to about 1100 nm. In some instance, fiber laser oscillator 38 may include one or more diffractive elements that narrow the linewidth of the emitted electromagnetic radiation. The linewidth of the electromagnetic radiation may be narrowed by the one or more diffractive elements to about 1080 nm. In one implementation, the one or more diffractive elements may include one or more Bragg gratings.

Isolator 40 may be located between fiber laser oscillator 38 and amplitude modulator 42. Isolator 40 may protect fiber laser oscillator 38 from undesired feedback.

Amplitude modulator 42 may include a high frequency acousto-optical modulator and may be controlled by an amplitude modulator driver executed by generation module 28 (shown in FIG. 1). As was mentioned above, amplitude modulator 42 may chop a beam of electromagnetic radiation received from fiber laser oscillator 38 into a train of pulses of electromagnetic radiation. The train of pulses may form a quasi-continuous wave beam of electromagnetic radiation that may eventually be delivered to the patient by output assembly 14. The pulses formed by amplitude modulator 42 may have a predetermined frequency and/or a predetermined pulse width. The predetermined frequency may be between about 0.1 kHz and about 1000 kHz. In one implementation, the predetermined frequency may be between about 5 kHz and about 100 kHz. The predetermined pulse width may be between about 0.1 ns and about 100 ns. In one implementation, the predetermined pulse width may be between less than about 30 ns. Due in part to the predetermined frequency and/or predetermine pulse width, in combination with subsequent processing of the electromagnetic radiation in the pulses (e.g., by amplification assembly 24 and wavelength adjustment assembly 26), the electromagnetic radiation in the pulses may eventually be delivered to the patient with a predetermined pulse fluence and/or a predetermined peak power. In some instances, the predetermined pulse fluence may be between about 250 mJ/cm$^2$ and 1000 mJ/cm$^2$. In some implementations, the predetermined peak power may be between about 50 kW and about 100 kW.

Figure 3:
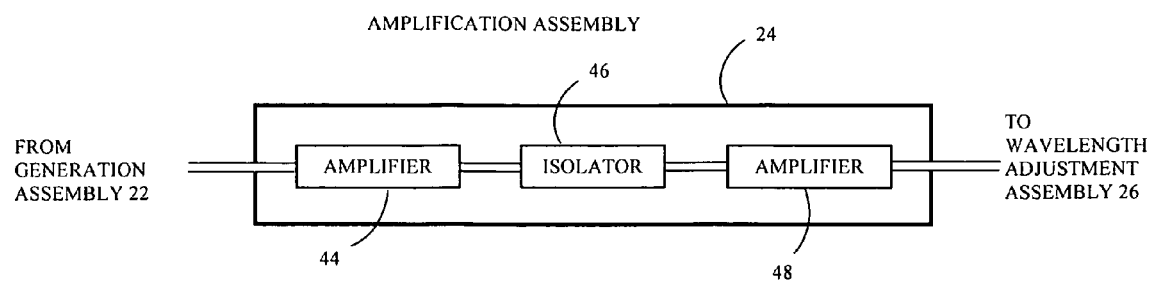
FIG. 3 illustrates an amplification assembly, in accordance with one or more embodiments of the invention.

Turning to FIG. 3, amplification module 24 is illustrated, according to one or more implementations. As can be seen, amplification module 24 may form a multi-stage amplifier system. The multi-stage amplifier system may include a first amplifier 44, an isolator 46, a second amplifier 48, and/or other components. First amplifier 44 may receive electromagnetic radiation at the fundamental wavelength and the fundamental power from source generation assembly 22, and may amplify the power of the received electromagnetic radiation.

Second amplifier 48 may be optically coupled to first amplifier 44, via isolator 46, to receive the electromagnetic radiation amplified by first amplifier 44. Second amplifier 48 may amplify the power of the received electromagnetic radiation. In some instances (not shown), the multi-stage amplifier system may include more (e.g., three or more) amplifiers than the amount shown in FIG. 3. In other instances, amplification module 24 may include only a single amplification stage.

Isolator 46 may be located between first amplifier 44 and second amplifier 46. Isolator 46 may protect first amplifier 44 from undesired feedback.

In some implementations of the invention, first and second amplifiers 44 and 48 may be formed as high-power, high-gain fiber amplifiers. In these implementations, amplifiers 44 and 48 may include large core Yb-doped fiber amplifiers. First and second amplifiers 44 and 48 may be controlled by a corresponding driver or drivers executed by amplification module 30 (as shown in FIG. 1) to provide the electromagnetic radiation received from generation assembly 24 with a predetermined gain.

The use of amplification assembly 24 in conjunction with generation assembly 22 may further enhance the power conversion efficiency of system 10 in providing electromagnetic radiation to output assembly 14. In some implementations, system 10 may convert the input power used by power assembly 16 to power system 10 to optical power output to the patient via output assembly 14 with an efficiency of greater than about 6%. In some of these implementations, the input power may be converted with an efficiency of between about 8% and about 14%.

Figure 4:
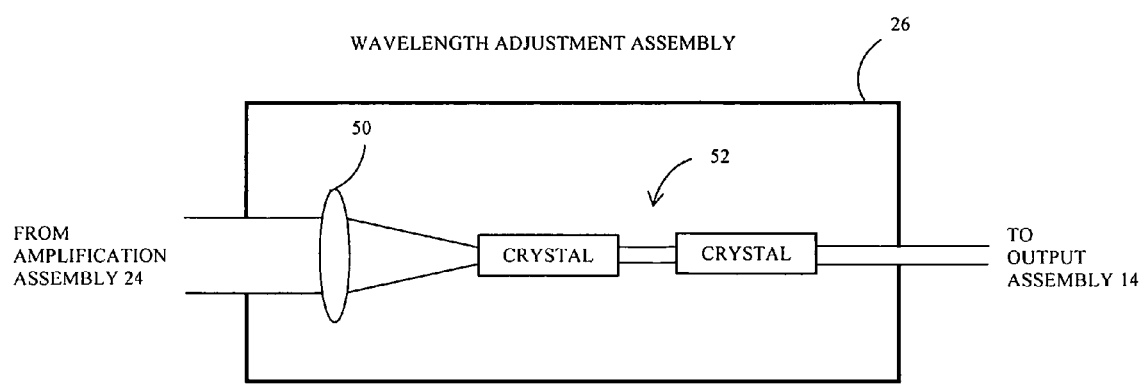
FIG. 4 illustrates a wavelength adjustment assembly, according to one or more embodiments of the invention.

FIG. 4 illustrates wavelength adjustment assembly 26, in accordance with one or more implementations. In the implementation(s) of FIG. 4, wavelength adjustment assembly 26 may include a refractive optical element 50 and a pair of crystals 52. Refractive optical element 50 may include a focusing lens that may concentrate electromagnetic radiation received by wavelength adjustment assembly 26 onto crystals 52. Crystals 52 may adjust the wavelength of the received electromagnetic radiation. Wavelength adjustment assembly 26 may act as a second harmonics generator by receiving electromagnetic radiation from amplification assembly 24 and adjusting the wavelength of the received electromagnetic radiation from the fundamental wavelength to the output wavelength. In some instances, wavelength adjustment assembly 26 may effectively half the wavelength (e.g., double the frequency) of the received electromagnetic radiation.

Crystals 52 may include nonlinear crystals arranged in a cascading configuration. Crystals 52 may be replaced by a single crystal, provided the single crystal is made long enough. Crystals 52 may be composed of a nonlinear material such as KTP or LBO. LBO may be more resistant to heat, and thus may be more compatible with use in wavelength adjustment assembly 26.

Figure 5:
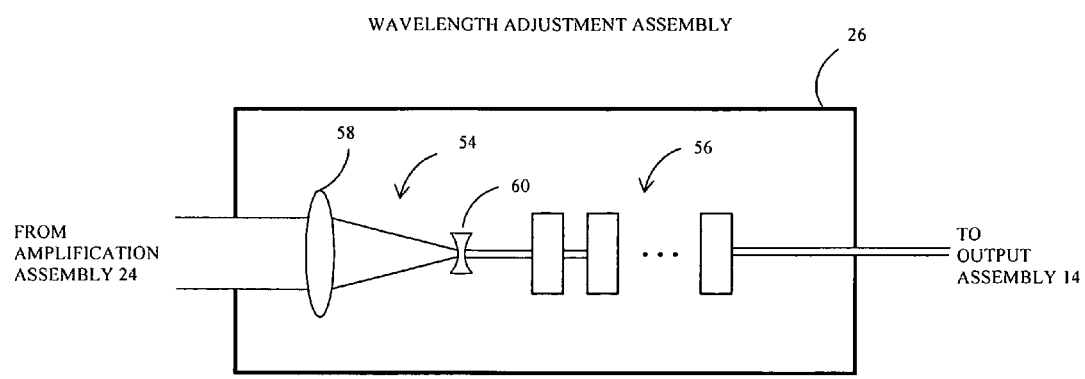
FIG. 5 illustrates a wavelength adjustment assembly, according to one or more embodiments of the invention.

Turning to FIG. 5, an illustration of one or more alternate implementations of wavelength adjustment module 26 is shown. In the implementation(s) of FIG. 5, wavelength adjustment module 26 may perform substantially the same function as the implementation(s) described above with respect to FIG. 4. However, in the implementation(s) of FIG. 5, wavelength module 26 may include collimating optics 54, a crystal array 56, and/or other components.

Collimating optics 54 may include a positive lens 58 and a negative lens 60. Collimating optics 54 may down collimate electromagnetic radiation received from amplification assembly 24. Down collimating the electromagnetic radiation may enable the beam size of the electromagnetic radiation to be reduced. This reduction in beam size may enhance the efficiency of adjustment of the wavelength.

Crystal array 56 may include a block array of a plurality of individual crystals 58. In some implementations, crystal array 56 may include three or more crystals. The crystals may be phase matched. For instance, the crystals may be type I or type II phase matched. The optical surfaces of the crystals may be coated with an anti-reflection coating for one or both of infrared and visible electromagnetic radiation.

In some implementations, the phase matched crystals in crystal array 56 may be mechanically and/or temperature tuned to meet the phase matching condition for the linewidth of the electromagnetic radiation emitted by fiber laser oscillator 38 to enhance the adjustment of the wavelength of the electromagnetic radiation (e.g., frequency doubling from near infrared to green). In some instances, this tuning may be monitored and controlled by temperature tuning module 34 (as shown in FIG. 1). The conversion efficiency of wavelength adjustment module 26, due at least in part to the temperature and/or mechanical tuning of the crystals in crystal array 56, may be greater than about 50%.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A surgical system that ablates soft tissue, the system comprising:
    a fiber laser oscillator;
    one or more pumping sources configured to provide pump energy to the fiber laser oscillator such that the fiber laser oscillator lases to emit electromagnetic radiation with a predetermined fundamental wavelength;
    one or more optical fiber amplifiers configured to (i) receive at least a portion of the electromagnetic radiation emitted by the fiber laser oscillator and (ii) amplify the received electromagnetic radiation;
    a second harmonics generator optically coupled to the one or more optical amplifiers to receive electromagnetic radiation that has been emitted by the fiber laser oscillator and amplified by the one or more optical amplifiers, wherein the second harmonics generator is configured to convert the wavelength of the received electromagnetic radiation from the predetermined fundamental wavelength to a predetermined output wavelength;
    an optical output configured to (i) receive electromagnetic radiation with the predetermined output wavelength that has been amplified by the one or more optical fiber amplifiers and (ii) deliver the received electromagnetic radiation to soft tissue of a patient to ablate the soft tissue; and
    a power assembly configured to receive an input power from an external power source sufficient to drive at least the one or more pumping sources and the one or more optical amplifiers with the input power,
    wherein the efficiency of the power of the electromagnetic radiation delivered to the soft tissue of the patient to ablate the soft tissue with respect to the input power is greater than about 6%.

2. The system of claim 1, wherein the one or more pumping sources comprise one or more diode lasers configured to deliver pump energy in the form of electromagnetic radiation to the fiber laser oscillator.

3. The system of claim 1, further comprising one or more diffractive elements within the fiber laser oscillator configured to provide the electromagnetic radiation emitted by the fiber laser oscillator with narrowed linewidth at the fundamental wavelength.

4. The system of claim 3, wherein the one or more diffractive elements comprise one or more Bragg gratings.

5. The system of claim 1, further comprising collimating optics configured to down-collimate electromagnetic radiation emitted by the fiber laser oscillator to reduce the beam size of the electromagnetic radiation received by the optical output.

6. The system of claim 1, wherein the collimating optics are arranged within the system to receive electromagnetic radiation that has been amplified by the one or more optical fiber amplifiers for down-collimation.

7. The system of claim 1, further comprising an amplitude modulator configured to (i) receive at least a portion of the electromagnetic radiation emitted by the fiber laser oscillator and (ii) modulate the amplitude of the received electromagnetic radiation to provide pulses of electromagnetic radiation at a predetermined pulse frequency with a predetermined pulse width.

8. The system of claim 7, wherein the predetermined pulse frequency is between about 0.1 kHz and about 1000 kHz.

9. The system of claim 7, wherein the predetermined pulse width is between about 0.1 nanosecond and about 100 nanoseconds.

10. The system of claim 1, wherein the second harmonics generator comprises one or more optical elements that down collimate the electromagnetic radiation received by the second harmonics generator.

11. The system of claim 1, wherein the fundamental wavelength is between about 900 nm to about 1200 nm.

12. The system of claim 1, wherein the output wavelength is between about 450nm and about 600 nm.

13. A surgical system that outputs electromagnetic radiation for ablating soft tissue, the system comprising:
    a generation assembly configured to generate electromagnetic radiation at a predetermined fundamental wavelength and a predetermined fundamental power, the generation assembly comprising one or more fiber laser oscillators that emit electromagnetic radiation at the fundamental wavelength and the fundamental power;
    an amplification assembly positioned to receive electromagnetic radiation that has been generated by the generation assembly, the amplification assembly comprising a plurality of optical fiber amplifiers configured to amplify the power of the received electromagnetic radiation;
    a wavelength adjustment assembly positioned to receive electromagnetic radiation generated by the generation assembly, the wavelength adjustment assembly being configured to adjust the wavelength of the received electromagnetic radiation such that electromagnetic radiation that is output by the system has a predetermined output wavelength that is shorter than the fundamental wavelength;
    an output assembly positioned to receive electromagnetic radiation that has at the output wavelength that has been amplified by the amplification assembly and configured to output the received electromagnetic radiation to soft tissue of a patient to ablate the soft tissue; and
    a power assembly configured to receive an input power from an external power source sufficient to drive at least the generation assembly and the amplification assembly, and wherein the power assembly is further configured to drive at least the generation assembly and the amplification assembly with the input power,
    wherein the efficiency of the power of the output electromagnetic radiation with respect to the input power is greater than about 6%.

14. The system of claim 13, wherein the efficiency of the amplified power with respect to the input power is between about 8% and about 14%.

15. The system of claim 13, further comprising collimating optics configured to down-collimate electromagnetic radiation emitted by the generation assembly to reduce the beam size of the electromagnetic radiation received by the output assembly.

16. The system of claim 13, further comprising a cooling assembly that primarily implements air cooling to cool the system.

17. The system of claim 13, wherein the power assembly is configured to receive substantially all of the input power from a standard wall outlet.

* * * * *